United States Patent
Bom

[11] 3,938,502
[45] Feb. 17, 1976

[54] APPARATUS WITH A CATHETER FOR EXAMINING HOLLOW ORGANS OR BODIES WITH THE ULTRASONIC WAVES

[76] Inventor: Nicolaas Bom, Weidebloemstraat 33, Berkenwoude (Z.H.), Netherlands

[22] Filed: May 9, 1974

[21] Appl. No.: 468,544

Related U.S. Application Data

[62] Division of Ser. No. 334,300, Feb. 21, 1973, Pat. No. 3,827,115.

[30] Foreign Application Priority Data
Feb. 22, 1972  Netherlands .................. 7202282
Mar. 10, 1972  Netherlands .................. 7203176

[52] U.S. Cl. ............ 128/2 V; 73/67.8 S; 128/2.05 Z
[51] Int. Cl.² .................................. A61B 10/00
[58] Field of Search ............ 128/2 V, 2.05 Z, 24 A; 73/67.8 R, 67.8 S, 67.9

[56] References Cited
UNITED STATES PATENTS

| | | | |
|---|---|---|---|
| 3,542,014 | 11/1970 | Peronneau | 128/2 V |
| 3,779,234 | 12/1973 | Eggleton et al. | 128/2 V |
| 3,789,833 | 2/1974 | Bom | 128/2 V |
| 3,805,596 | 4/1974 | Klahr | 128/2 V |

OTHER PUBLICATIONS
Bom, N. et al., Ultrasonics, Mar. 1972, pp. 72–76.
Bom, N. et al., Bio–Medical Engnrg., Nov. 1971, Vol. 6, No. 11, pp. 500–503, 508.

*Primary Examiner*—Kyle L. Howell
*Attorney, Agent, or Firm*—Haseltine, Lake & Waters

[57] ABSTRACT

A device for examining the heart is provided with a catheter adapted to be placed within the heart and including at one end thereof, circumferentially arranged, equidistantly distributed elements, serving for the transmission and reception of ultrasonic waves. The catheter has an axis and the elements have no directivity in a plane perpendicular to this axis. The elements are so dimensioned in axial direction that in a plane through the axis they do show directivity. An excitation device is provided which successively excites groups of adjacently arranged elements and time delays are provided for delaying the transmitted and received pulses for the elements of a group that the differences in travel times are compensated. An adder is provided for the summation of echo pulses and a device is provided for visually displaying the part of the examined heart surrounding the catheter.

19 Claims, 12 Drawing Figures

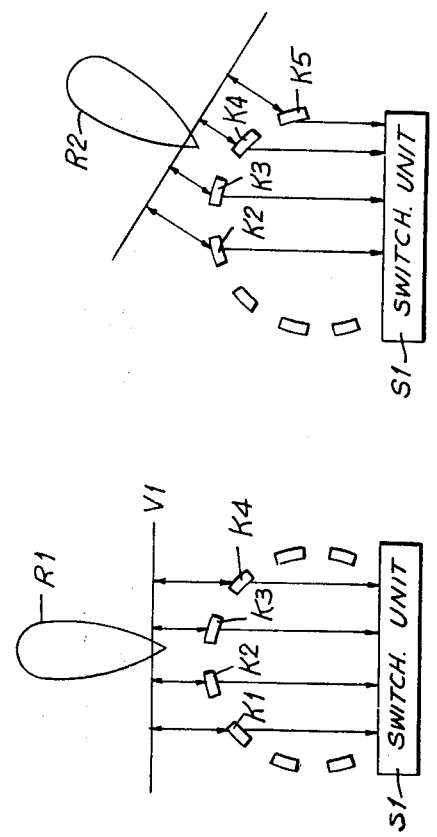
FIG. 3
FIG. 2
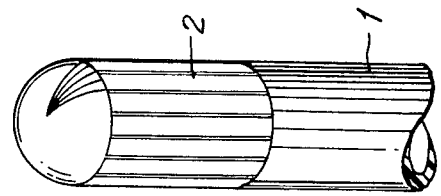
FIG. 1

FIG. 7
FIG. 8
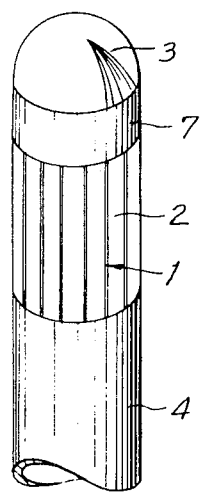
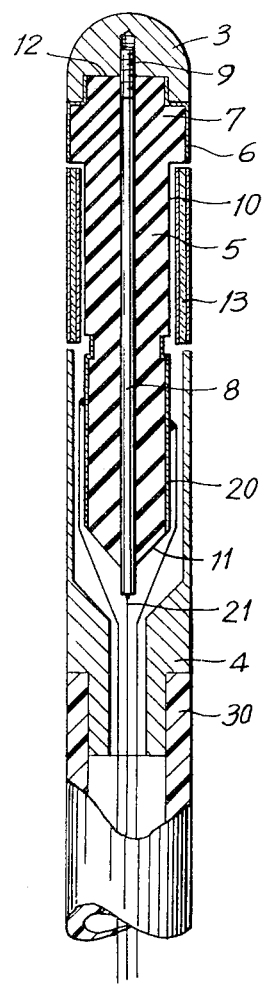

APPARATUS WITH A CATHETER FOR EXAMINING HOLLOW ORGANS OR BODIES WITH THE ULTRASONIC WAVES

This Application is a divsion of application Ser. No. 334,300 filed Feb. 21, 1973, now U.S. Pat. No. 3,827,115, and claims the priority of my Applications filed in the Netherlands on Feb. 22, 1972 and Mar. 10, 1972.

FIELD OF INVENTION

This invention relates to devices for examining a hollow organ, such as the heart, which devices are of the type which comprises a catheter which is to be placed inside the hollow organ and which is provided at its end with circumferentially arranged, equidistantly distributed elements, each of which serves both for the transmission and the reception of ultransonic waves.

BACKGROUND

A device of the type indicated above has been previously proposed comprising an intracardiac catheter provided near its end with four elements for the transmission of ultrasonic waves, which elements are spaced equiangularly apart at 90° intervals and which each have some directivity. With the aid of this catheter, it is possible to transmit ultransonic waves in four different directions and to determine the distance to the heart wall from the time interval between the excitation of the elements and the reception of the echo pulse. If the entire heart wall is to be scanned, the catheter must be rotated about is axis, a procedure which is difficult to realize. It will therefore be clear that, with this catheter, it is not possible at any moment to completely visualize moving cardiac structures, such as heart walls and heart valves, surrounding the catheter. In principle, it would be possible to determine the dimensions of the heart in a larger number of directions by providing the catheter with a larger number of elements.

Techniques for determining the distance from object in one of a larger number of directions around an ultrasonic source are known in themselves from Sonar (Bom, Lancee, Algemene inleiding tot de echocardiografie, Het Ingeniemsblad, No. 3, 1972, p. 3–6). The possibility of applying Sonar Techniques to a heart catheter has also been touched upon in a paper presented to the British Medical Ultrasonics Group, at Glasgow, Great-Britain, Dec. 10, 1971, (Bom, Lancee, Technical Developments in echocardiographic apparatus). However, the dimensioning of the ultrasonic equipment for Sonar is such that without difficulty it can be provided with a large number of elements.

In contrast to the situation with Sonar, however, the dimensions permissible for a catheter are in the order of magnitude of millimeters, thus limiting the number of directional elements at the frequencies used for diagnostic purposes.

SUMMARY OF INVENTION

An object of the invention is to avoid this drawback and to provide a device with which the dimensions of a hollow organ can be determined in a large number of directions without it being necessary for the catheter to be rotated for this purpose.

The invention, moreover, provides a device with which it is possible at any moment to obtain a complete cross-sectional view of the part of the examined hollow organ surrounding the catheter. The device according to the invention is characterized by a large number of elements which show very little directivity in a plane perpendicular to the axis of the catheter, the elements being so dimensioned in axial direction that the major part of the acoustic energy in transmission is confined to a plane perpendicular to the axis of the catheter. An excitation device is further provided which successively excites groups of adjacently arranged elements at a rate of at least 15 times per second. There are time delays for so delaying the transmitted and the received pulses for the elements of a group that the differences in travel times among the elements for the pulses to or from a line lying in the plane perpendicular to the catheter axis and being, perpendicular to the center line of the group, are compensated. There is further an adder for the summation of the echo pulses brought into coincidence by the time delays. A device is used for visually displaying the part of the examined hollow organ surrounding the catheter, which device is controlled by the adder.

The groups of elements excited in successive cycles are preferably moved up one element with respect to each other. Moreover, it is preferred that each group consists of an even number of elements. The elements of a group are preferably divided into pairs of elements positioned symmetrically with respect to the center line, communal time delays being used for each pair both in the transmitting circuit and in the receiving circuit.

In one embodiment of the invention, all groups are gone through 150 to 200 times per second, so that also the heart structures moving fastest can be continuously observed on the screen of a cathode ray tube.

The frequency of the ultrasonic waves is preferably in the range of 5–6 MHz and the number of elements may be, for instance, 30 to 40.

The selection of the groups is preferably effected by two electronic switching units which are controlled by a clock generator, one switching unit serving to excite the elements and the other to feed the echo pulses to a processing circuit. It is preferred that, from each clock pulse, a starting pulse is derived which via appropriate time delays controls the generators for the excitation, the echo pulses being fed via appropriate time delays to an adder which sums the coinciding echo pulses. As the strength of the echoes is dependent on the distance covered, it is recommended that the output signals are fed from the adder to an amplifier with a time-dependent amplification factor, which amplifier is controlled by the clock generator, as a result of which the differences in strength are compensated.

In order to make it possible for the catheter to be introduced into the hollow organ to be examined, it must in many cases have a diameter of not more than a few mm. As a result, extremely high demands are made on the manufacture thereof, particularly considering that within this small diameter a large number of elements are to be accommodated.

The device according to the invention can be manufactured by a method which provides a very satisfactory solution to this manufacturing problem. It is characterized in that the basic member is a substantially cylindrical core of insulating material, the outer surface of which is provided with a layer of conductive material which, by locally removing this material, is divided into two sections, a front and rear section, respectively, which are insulated from each other and in that, on part of the outer surface of said core, a hollow cylinder of piezoelectric material is placed, which cylinder is so polarized that in radial direction a thickness resonance takes place for the ultrasonic waves to be generated, the two cylinder surfaces being provided with electrodes in the form of layers, which are each connected to one of the sections of the conductive layer on the core, after which the piezoelectric cylinder and the outer part of the core are sawn through along a number of radial planes interspaced at equal angular distances, so that a number of separate elements are formed, one of the electrodes of each element being connected via the corresponding part of the conductive layer of the core to a corresponding feed wire and the other electrode being connected via the other part of the conductive layer to a communal conductor.

In an effective embodiment of the invention, the core is provided with a central bore through which either the communal conductor or the separate feed wires are passed. If the communal conductor is passed through the bore, it may be connected to the outer electrodes of the elements by means of a metal cap, which is attached to the leading end of the catheter.

If initially the conductive layer extends over the entire outer surface of the core, it must be removed from the end face on the side of the separate feed wires in order to prevent a short circuit between these wires.

In one form according to the invention, the piezoelectric cylinder is bonded to the core by means of an adhesive. Connecting the electrodes of the piezoelectric cylinder to the two parts of the conductive layer of the core may with advantage be done by soldering.

The catheter according to the invention may be connect to the catheter tube by means of a coupling member which engages with the rear part of the core. It is also effective that the core is at its leading end provided with an expanded part whose diameter is equal to the outer diameter of the piezoelectric cylinder.

In order to reduce cross-talk between the various elements to a minimum, it is recommended that the feed wires be passed through the catheter tube in bundles, care being taken that the feed wires of each group of elements all belong to different bundles.

For the sawing through of the piezoelectric cylinder and the outer part of the core, there are two methods. With the first method use is made of a circular saw and the core is provided with an end piece which during sawing may be clamped on the core and later on removed therefrom. With the second method use is made of a metal wire and the core is fixed between centers which are preferably formed by the ends of the communal conductor passing through the central bore of the core.

After the catheter has been made, it is preferably covered with a thin protective layer. For the acoustic matching of the object to be examined, it is of advantage to give said layer a thickness of ¼ wave length, said layer preferably being of a material having a basis of expoxy-resin.

BRIEF DESCRIPTION OF DRAWING

The invention is next further explained with reference to the accompanying drawing, which shows a few embodiments. In the drawing:

FIG. 1 is a view in perspective of a catheter used for the device according to the invention;

FIGS. 2 and 3 illustrate the directivity obtained by group-wise excitation of the transmitting elements;

Figure 9:
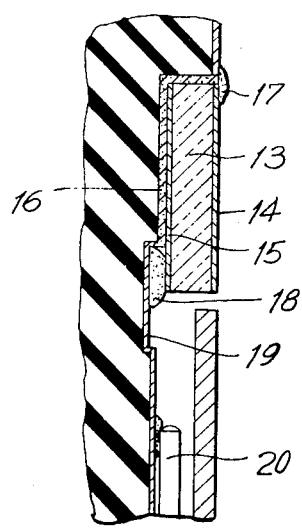
Figure 10:
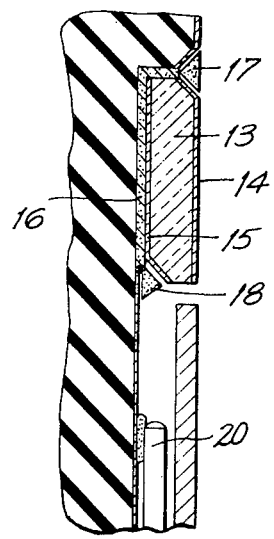
Figure 11:
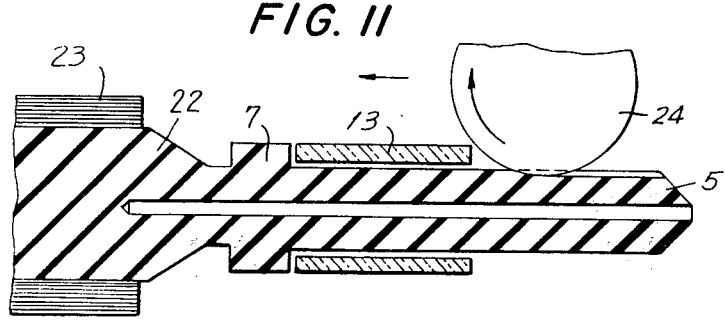
Figure 12:
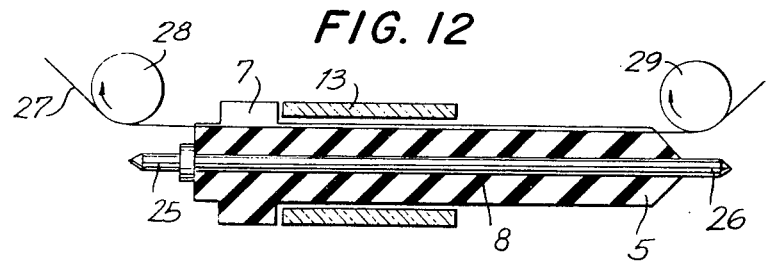

The method of manufacturing the catheter is illustrated in FIGS. 7–12 as follows:

FIG. 7 shows a catheter made according to the invention;

FIG. 8 is a longitudinal section of the catheter according to FIG. 7;

FIG. 9 shows a detail of the catheter according to FIG. 8;

FIG. 10 shows a variant of the construction according to FIG. 9;

FIG. 11 shows the sawing through of the piezoelectric cylinder with the aid of a circular saw; and FIG. 12 shows the sawing through of the piezoelectric cylinder with the aid of a metal wire.

DETAILED DESCRIPTION

The catheter shown in FIG. 1 consists of a cylindrical body 1 containing a number of circumferentially arranged piezoelectric crystals or elements 2 which are insulated from each other and resonate in radial direction at the frequency of the ultrasonic waves. These crystals have such a length that the sound is substantially confined to a plane perpendicular to the longitudinal axis of the cylindrical body 1.

FIG. 2 schematically shows the operation of the device during a first cycle. During this cycle the crystals K1–K4 are excited.

The crystals may be considered to be line source transmitters which emit sound waves in all radial directions. The distances from the crystals to a plane V1 positioned perpendicular to the center line of the group of crystals vary; namely for the crystals K1 and K4 the distance is longer than for the crystals K2 and K3. When the crystals are excited simultaneously, the echo pulses coming in parallel to the center line are consequently received at different moments. According to the invention, this difference in travel time is compensated by means of time delays, so that for the direction parallel to the center line of the group coinciding echo pulses are received which are added. As a result, a particularly strong sum signal is formed for the echo pulses coming in parallel to the center line. For echo pulses that come in from other directions, the differences in travel time have not been compensated so that the sum pulse for these echo pulses is considerably smaller. The resulting directivity is schematically referred to by the directional characteristic R1.

During the subsequent, cycle, which is illustrated in FIG. 3, the crystals K2–K5 are excited, resulting in a directivity referred to by the directional characteristic R2.

By having the group of excited crystals moved up one crystal position after each cycle, there will be obtained a rotating directional characteristic with which the entire circumference of the hollow organ can be scanned.

Figure 4:
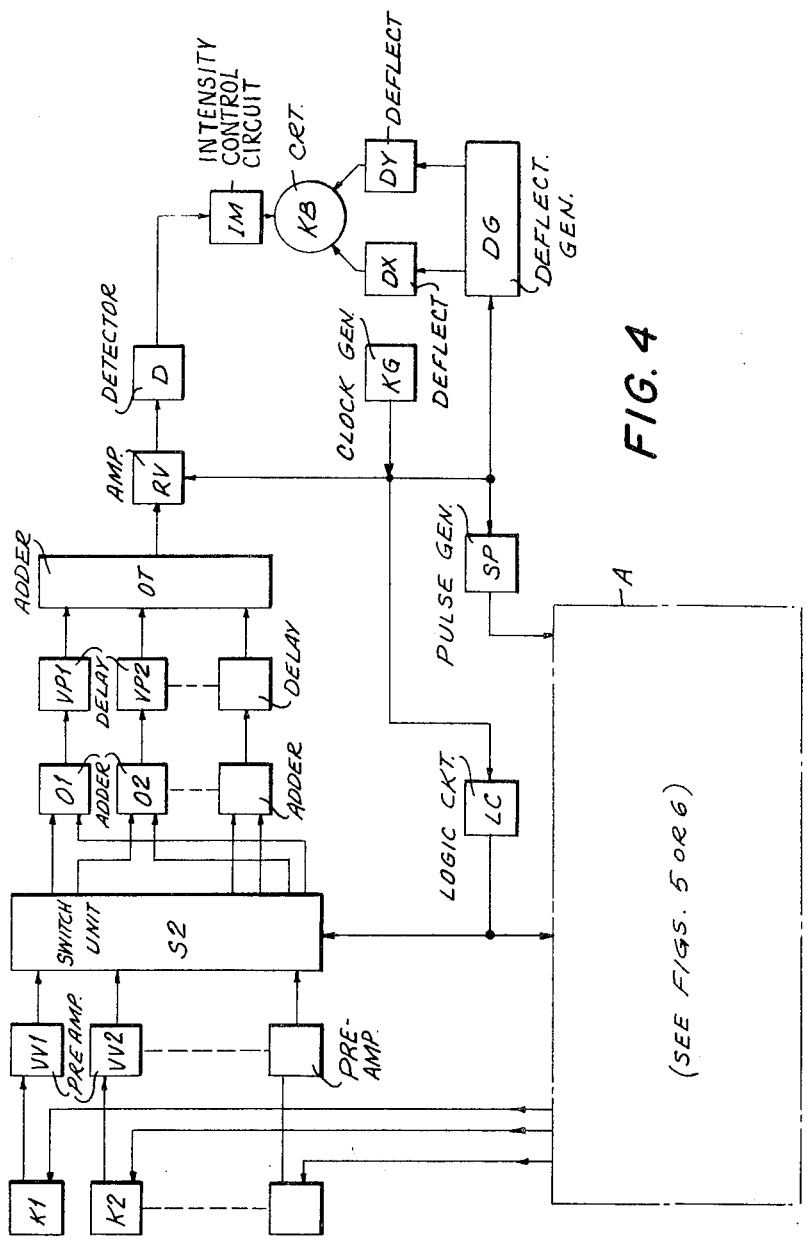
FIG. 4 is a block diagram of a device according to the invention.

The device illustrated in FIG. 4 is controlled by a clock generator KG. This clock generator controls a logic circuit LC, which serves to select the groups, and also controls a pulse generator SP, which initiates the excitation of the crystals of the group selected. The generation of the excitation pulses and the distribution of these pulses over the crystals of the selected group is effected by means of a device A, which may be constructed in two different ways.

Figure 5:
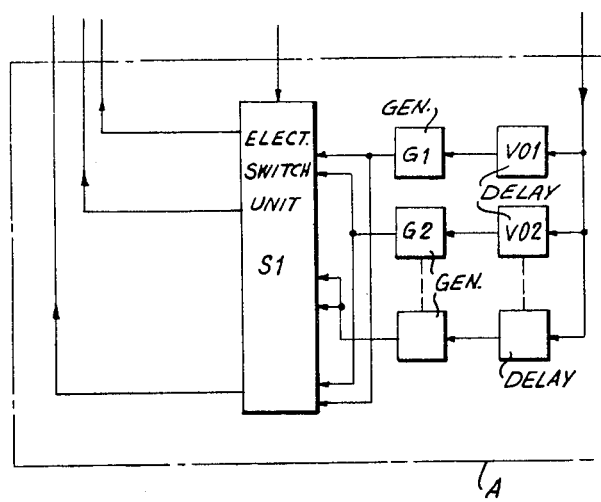
FIGS. 5 and 6 are block diagrams of two variants of a detail of the device according to FIG. 4.

In the construction represented in FIG. 5 the starting pulse is fed to a series of delays V01, V02, etc. which each control a respective generator G1, G2. The pulses of each generator are fed to two inputs of the electronic switching unit S1, which is controlled by the logic circuit LC, which inputs belong to elements positioned symmetrically with respect to the center line of the group. The outputs of the switching unit S1 are connected to the crystals K1, K2, etc. respectively.

Figure 6:
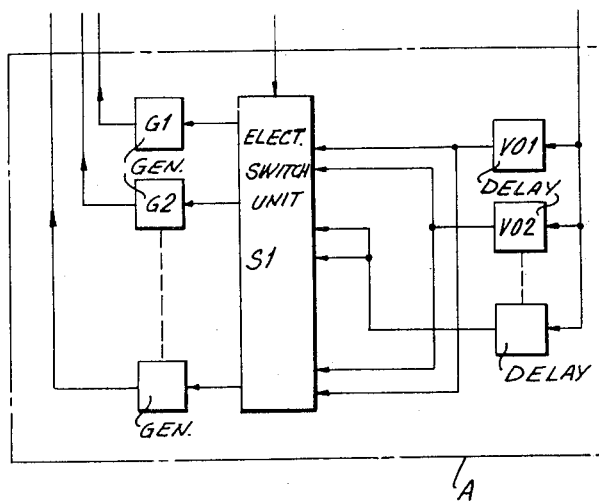

In the construction according to FIG. 6, the output pulses of the delays V01, V02, etc. are directly fed to the switching unit S1, the outputs of which are connected to a corresponding generator G1, G2, etc., each of which generators now excites one corresponding crystal.

According to FIG. 4 the echo pulses received by the crystals are fed via preamplifiers VV1, VV2, etc, to a second switching unit S2, which is also controlled by the logic circuit LC. The echo pulses received from the crystals positioned symmetrically with respect to the center line of the group are fed by the switching unit S2 respectively to adders 01, 02 etc., which add the respective pulses. The output signal from each adder is fed to a time delay VP1, VP2 etc. which cause such a delay that, of the echo pulses coming in parallel to the center line of the group, the coinciding pulses are fed to the adder OT. The output pulses from the adder OT pass through an amplifier RV whose amplification factor increases as a function of time and which amplifier is controlled by the clock generator KG. As a result, the difference in strength as a function of the travel distance is compensated. Via the detector D, the signal received is fed to an organ IM, which controls the intensity of the cathode ray of a cathode-ray tube KB. The deflection members DX and DY of this cathode-ray tube are controlled by a deflection generator DG, which is connected to the clock generator KG. The deflection generator causes the cathode ray to be radially deflected from the center of the cathode-ray tube, the direction of the ray always corresponding to the center line of the selected group. In this way, a picture of the moving wall of the hollow organ examined is displayed on the screen of the cathode-ray tube.

The number of elements may be 32, the clock frequency being so selected that all groups are scanned about 160 times per second. This scanning frequency is so high that the eye will observe a continuous picture of the fastest moving heart structures. A suitable frequency of the ultrasonic waves is 5–6 MHz.

The manufacture of the catheter will now be illustrated with reference to the FIGS. 7–12.

In the catheter 1 according to FIG. 7 are a number of circumferentially arranged piezoelectric crystals 2. There may be, for instance, thirty-two or thirty-six of these elements. At the leading end, the catheter may be closed by a metal cap 3. The catheter is connected to a normal catheter tube by means of a coupling member 4.

The manufacture of such a catheter will be illustrated with reference to FIG. 8. The basic member in the manufacture is a substantially cylindrical core 5 of insulating material, which is covered with a conductive layer 6. The core may consist of, for instance, a synthetic material of the ABS-type, in which case the conductive layer may be applied in three stages, namely by applying a copper coating, which may be done chemically, and electroplating with a coating of nickel, and electroplating with a coating of gold. The total thickness of the layer may be about 40 microns.

It is also possible for the core to be made of epoxy resin to which a thin coating of aluminum may be applied by vaporization. At its leading end, the core is provided with an expanded portion 7 whose diameter is equal to the outer diameter of the circular array of elements to be provided. In the core, there is made a central bore in which a conductor 8 is secured which is at its leading end provided with a screw thread 9, with the aid of which the cap 3 is secured to the catheter. The conductive layer 6 is removed from a part 10 of the outer surface of the core on which the elements are to be placed, and from the conical end surface 11. If necessary, the conductive layer is also removed from the flat end face 12. It is also possible to use embodiments in which the core is initially provided with an end piece which is later on sawn off, in which case no conductive layer is present on the end face 12.

After the conductive layer in the above-indicated zones has been removed, a hollow cylinder 13 is placed on the core, which hollow cylinder is of a piezoelectric material and so polarized that, in radial direction, resonance will take place for the sound waves to be generated. The cylinder 13 is on its inner surface and on its outer surface provided with electrodes 14 and 15 in the form of a layer (see FIGS. 9 and lo)--. The cylinder 13 is bonded to the core by means of an adhesive 16. The outer electrode is soldered (17) to the leading part of the conductive layer of the core near the end of the catheter, whereas the electrode 15 is soldered (18) to the rear part of the conductive layer remote from the free catheter end. In order to facilitate soldering at said last-mentioned point, the core is locally provided with a groove 19.

It should be added that, in the construction according to FIG. 10, both ends of the piezoelectric cylinder 13 are bevelled as a result of which the solder 17 and 18 will come to lie within the circumference of the cylinder 13. There is no need then for the groove 19.

FIGS. 11 and 12 show two different methods of dividing the hollow cylinder 13 of piezoelectric material into a large number of separate elements.

With the method according to FIG. 11, the core 5, on which the hollow cylinder 13 is placed, is fixed in a clamp 23. The core 5 already contains the central conductor 8 (see FIG. 8). Subsequently, an extremely thin, rotating diamond saw 24 is passed through the cylinder 13 in axial direction (see the horizontal arrow in FIG. 11). In the cylinder 13, a saw cut is formed having a width which may be in the range of 100 to 140 $\mu$. The depth of cut of the diamond saw is such that it also just removes the conductive layer 6 (see FIG. 8) which is on the part of the core 5 opposite the inner wall of the coupling member 4.

After each saw cut, the core 5 with the hollow cylinder 13 is turned through a particular angle, depending on the number of elements to be provided. After having thus divided this cylinder 13 into the desired number of elements, part of the core 5 is sawn off in radial direction at 22.

With the method according to FIG. 12, the core 5, with the cylinder 13 on it, is clamped up by means of the centering ends 25 and 26 of the central conductor 8. The cylinder 13 is now grooved with the aid of a hard metal cutting wire 27 which is guided by the rollers 28 and 29. The grooving is done by causing the workpiece 5, 13 to make a translation in the direction of the cutting wire 27 or by moving the cutting device 27, 28, 29 to the workpiece 5, 13.

On each of the sectors into which the conductive layer 6 has been cut at its rear end, a feed wire 20 is placed, which also may be done by soldering, as indicated in FIGS. 9 and 10. Each feed wire belongs to one particular element. A feed wire 21 is attached to the conductor 8 in the central bore of the core.

Subsequently, the metal end cap 3 is screwed on the conductor 8, as a result of which the outer electrodes of all the elements are connected to the feed wire 21. The catheter is connected to a catheter tube 30 of the usual construction by means of a coupling member 4, which engages with the rear part of the core 5. The feed wires 20 and 21 are passed through the catheter tube 30.

The feed wires 20 are assembled in a number of bundle which preferably each comprise a ground conductor, care being taken that the feed wires 20 of each group of elements all belong to different bundles. In this way the cross-talk between the various elements, which also act as receivers of the echo pulses, is reduced to a minimum.

The feed wire 21 is connected to ground, so that the outer electrodes of all the elements are grounded. In this way, the risk run by a patient is reduced to a minimum.

The catheter is finished by covering it with a thin protective coating, which may be done by repeatedly immersing it in a solution of polyurethane in a mixture of dioxan and tetrahydrofuran. In this way, a sealing coat is obtained which does not attack the blood or the tissue of the patient examined.

In order to match the acoustic impedance with that of the object to be examined, it may be of advantage to use a protective layer of a material having a basis of epoxy-resin, said layer having a thickness of ¼ wave length.

Connecting the electrodes of the piezoelectric cylinder to the feed wires can be done with the aid of a solder having a low melting temperature, for instance: 60–95°C, at which temperature the crystals are not depolarized, or by soldering for a very short time at a higher melting temperature or by making use of a conductive adhesive.

The catheter described is meant, in the first place, for examining the heart, the catheter being introduced into the heart through a blood vessel. An intracardiac catheter according to the invention was provided with 32 elements and had an external diameter of only 3 mm. Each element had a thickness d of 0.35 mm (in radial direction) and a length 1 of 5 mm (in axial direction of the catheter). However, the catheter may also be used for examining other hollow organs such as, for instance, the urinary bladder.

The above-described embodiment may still be varied within the scope of the invention. For instance, it is not essential that the end cap is attached to the catheter by means of a screw thread. For this purpose, use may be made of a different electrically conductive securing means. Furthermore, the provision of the central bore in the core for accommodating the connections is optional. Alternatively, the connections may be provided on the outside of the catheter.

What is claimed is:

1. A device for examining a hollow organ, such as the heart, said device comprising a catheter having an axis and adapted to be placed inside the follow organ and including at an end, at least four circumferentially arranged, equidistantly distributed elements, each of which is adapted for the transmission and the reception of ultrasonic waves in successive transmission-reception periods, each of said elements having a width in a plane perpendicular to the axis of the catheter which is smaller than the wavelength of the ultrasonic waves such that they show substantially no directivity in a plane perpendicular to the axis of the catheter, the elements haveing axial dimensions which are larger than said wavelength, such that they do show directivity in a plane containing the said axis; an excitation device which successively excites groups of adjacently arranged elements at a rate of at least 25 times per second, each group having a center line; time delays for delaying the pulses transmitted and received during a transmission-reception period by the elements of a group so that the differences in travel times among the elements for the pulses to or from a plane perpendicular to the center line of the group are compensated; an adder for the summation of the echo pulses brought into coincidence by the time delays; and means controlled by the adder, for visually displaying the part of the examined hollow organ surrounding the catheter.

2. A device as claimed in claim 1, said catheter comprising a plurality of conductive strips, a generally cylindrical core of insulating material, the said elements being disposed about the core, an inner electrode on each element electrically connected to a respective one of said conductive strips, said strips extending along the core away from the associated element towards one end portion of the core, a common conductive layer, and an outer electrode on each element electrically connected to said common conductive layer which is located on the other end portion of the core.

3. A device as claimed in claim 2, in which the core is provided with an axial passage comprising an electrical lead in said passage connected to the common conductive layer.

4. A device as claimed in claim 2 in which the core is provided with an axial passage, comprising a plurality of electrical leads in said passage connected to the said strips.

5. A device as claimed in claim 2, in which the core is provided with an axial passage, said device comprising a metal cap and further comprising an electrical conductor in said passage connected to said metal cap which is located at the tip of the catheter, said cap being in electrical contact with the said common conductive layer.

6. A device as claimed in claim 2 further comprising an adhesive and in which the elements are attached to the core by said adhesive.

7. A device as claimed in claim 2 further comprising solder and in which the electrodes are connected by the solder to the associated conductive strips and to the conductive layer.

8. A device as claimed in claim 2 in which the core includes a leading end and, at said leading end, a portion of external diameter equal to that of the circumferentially arranged elements.

9. A device as claimed in claim 2 in which the core includes a coupling member located at a rear end portion of the core and adapted to connect the core to a catheter tube.

10. A device as claimed in claim 1, in which the catheter includes a thin external protective coating.

11. A device as claimed in claim 10 in which the coating has a thickness of ¼ wave length relative to the said predetermined wavelength.

12. A device as claimed in claim 1 wherein each group consists of an even number of elements.

13. A device as claimed in claim 12, wherein the elements of a group are divided into pairs of elements positioned symmetrically with respect to the center line, the elements of each pair co-operating with common time delays both in transmitting and in receiving.

14. A device as claimed in claim 1 including thirty to forty of said elements.

15. A device as claimed in claim 1, wherein said excitation device comprises means adapted to move up the groups of successively excited adjacent elements by one element after each transmission-reception period.

16. A device as claimed in claim 1, wherein said excitation device comprises means for exciting all groups 150–200 times per second.

17. A device as claimed in claim 1, comprising two electronic switching units, a clock generator, and a processing circuit, the selection of the groups being effected by said two electronic switching units controlled by said clock generator which generates clock pulses therefore, one of said switching units serving to excite the elements and the other to feed the echo pulses to said processing circuit.

18. A device as claimed in claim 17, comprising means whereby from each clock pulse a starting pulse is derived which via selected of said time delays controls the excitation device, the echo pulses being fed via selected of said time delays to said adder which sums coinciding of the echo pulses.

19. A device according to claim 18, comprising an amplifier with a time-dependent amplification factor controlled by the clock generator, for the output signals from the adder.

* * * * *